United States Patent
Churchvara et al.

(10) Patent No.: US 9,285,792 B2
(45) Date of Patent: Mar. 15, 2016

(54) PROGRAMMABLE LOGIC CONTROLLER-BASED CONTROL CENTER AND USER INTERFACE FOR AIR SAMPLING IN CONTROLLED ENVIRONMENTS

(71) Applicant: Veltek Associates, Inc., Malvern, PA (US)

(72) Inventors: Jeffrey Churchvara, Downingtown, PA (US); Mark Phillips, King of Prussia, PA (US)

(73) Assignee: Veltek Associates, Inc., Malvern, PA (US)

( * ) Notice: Subject to any disclaimer, the term of this patent is extended or adjusted under 35 U.S.C. 154(b) by 0 days.

(21) Appl. No.: 13/673,523

(22) Filed: Nov. 9, 2012

(65) Prior Publication Data

US 2014/0132415 A1     May 15, 2014

(51) Int. Cl.
| | |
|---|---|
| G08B 21/00 | (2006.01) |
| G05B 19/02 | (2006.01) |
| G01M 3/28 | (2006.01) |
| G08B 21/12 | (2006.01) |

(52) U.S. Cl.
CPC ............. *G05B 19/02* (2013.01); *G01M 3/2815* (2013.01); *G08B 21/12* (2013.01)

(58) Field of Classification Search
CPC ......... G01N 1/26; G01N 1/2273; F24F 3/161; G05B 19/02; G08B 21/12; G08B 17/04; G01M 3/2815; G01F 1/42
USPC .......... 340/606, 609, 603; 73/863.03, 863.01, 73/863.02, 863; 454/187; 700/215–217
See application file for complete search history.

(56) References Cited

U.S. PATENT DOCUMENTS

| | | | |
|---|---|---|---|
| 4,091,674 A | 5/1978 | Amey | |
| 4,604,111 A | 8/1986 | Natale | |
| 4,663,293 A | 5/1987 | Hempel et al. | |
| 4,804,391 A | 2/1989 | Griffis | |
| 4,813,984 A | 3/1989 | Griffis | |
| 5,195,922 A * | 3/1993 | Genco | ............................ 454/57 |

(Continued)

FOREIGN PATENT DOCUMENTS

| | | |
|---|---|---|
| CN | 1598591 A | 3/2005 |
| EP | 2343528 A2 | 7/2011 |

(Continued)

OTHER PUBLICATIONS

Veltek Associates, Inc., One Touch Command (TM) SMA (TM) Microbial Air Sampling Systems Brochure, Revised Dec. 2002, 4 pgs., Malvern, Pennsylvania.

(Continued)

*Primary Examiner* — Anh V La
(74) *Attorney, Agent, or Firm* — Blank Rome LLP; Peter S. Weissman

(57) ABSTRACT

In accordance with an aspect of the present invention there is provided a system for sampling air at multiple locations in a controlled environment. The system includes one or more air sampling devices configured to monitor and test a volume of air within a controlled environment. A control center including a programmable logic controller (PLC) is configured to monitor and control the one or more air sampling devices. One or more touch panel displays are connected to the control center and provide a human-computer interface between the control center and users.

28 Claims, 3 Drawing Sheets

(56) References Cited

U.S. PATENT DOCUMENTS

| | | | |
|---|---|---|---|
| 5,421,214 | A | 6/1995 | Burgdorfer |
| 5,553,496 | A | 9/1996 | Nishiyama et al. |
| 5,645,480 | A | 7/1997 | Spengler |
| 5,831,182 | A | 11/1998 | Swenson |
| 5,838,008 | A | 11/1998 | Esler et al. |
| 6,125,710 | A | 10/2000 | Sharp |
| 6,167,107 | A | 12/2000 | Bates |
| 6,167,766 | B1 | 1/2001 | Dunn et al. |
| 6,216,548 | B1 | 4/2001 | Park et al. |
| 6,230,080 | B1 | 5/2001 | Lee et al. |
| 6,295,864 | B1 | 10/2001 | You et al. |
| 6,425,297 | B1 | 7/2002 | Sharp |
| 6,425,298 | B1 | 7/2002 | Jackson et al. |
| 6,514,721 | B2 | 2/2003 | Spurrell |
| 6,532,835 | B1 | 3/2003 | Saaski et al. |
| 6,692,953 | B1 | 2/2004 | Sugita et al. |
| 6,867,682 | B2 | 3/2005 | Reinhardt et al. |
| 7,127,847 | B2 * | 10/2006 | Fitzgibbon et al. ............... 49/28 |
| 7,667,839 | B2 | 2/2010 | Bates |
| 7,940,188 | B2 | 5/2011 | Calio et al. |
| 7,973,668 | B2 | 7/2011 | Calio et al. |
| 8,006,542 | B2 | 8/2011 | Jones, Jr. |
| 8,169,330 | B2 | 5/2012 | Calio et al. |
| 8,188,874 | B2 | 5/2012 | Calio |
| 8,199,003 | B2 * | 6/2012 | Aaron ..................... 340/539.26 |
| 8,494,481 | B1 * | 7/2013 | Bacco et al. ............... 455/404.1 |
| 8,701,980 | B2 | 4/2014 | Calio et al. |
| 2001/0030642 | A1 | 10/2001 | Sullivan et al. |
| 2002/0070862 | A1 | 6/2002 | Francis et al. |
| 2004/0044493 | A1 | 3/2004 | Coulthard |
| 2006/0000296 | A1 | 1/2006 | Salter |
| 2008/0148816 | A1 * | 6/2008 | Groves ........................ 73/31.01 |
| 2010/0289653 | A1 | 11/2010 | Calio et al. |
| 2011/0192213 | A1 | 8/2011 | Zimmerman et al. |
| 2012/0212342 | A1 | 8/2012 | Aaron |
| 2012/0218102 | A1 | 8/2012 | Bivens et al. |
| 2014/0132415 | A1 | 5/2014 | Churchvara et al. |

FOREIGN PATENT DOCUMENTS

| | | |
|---|---|---|
| WO | WO-2009100184 A1 | 8/2009 |
| WO | WO-2010105161 A1 | 9/2010 |
| WO | WO-2011103145 A1 | 8/2011 |

OTHER PUBLICATIONS

Search Report and Written Opinion of co-related PCT/US2010/027145 dated Apr. 27, 2010, 8 pages.

International Appl. No. PCT/US2009/033163, International Search Report and Written Opinion, dated Jun. 24, 2009, 7 pages.

International Appl. No. PCT/US2010/027145, International Search Report and Written Opinion, dated May 12, 2010, 10 pages.

International Appl. No. PCT/US2011/025021, International Search Report and Written Opinion, dated Mar. 17, 2011, 5 pages.

* cited by examiner

PROGRAMMABLE LOGIC CONTROLLER-BASED CONTROL CENTER AND USER INTERFACE FOR AIR SAMPLING IN CONTROLLED ENVIRONMENTS

FIELD OF INVENTION

The present invention relates to devices and methods for monitoring airborne contaminants. In particular, the present invention relates to a programmable logic controller-based control center and corresponding human computer interface for controlling air sampling in controlled environments.

BACKGROUND OF THE INVENTION

Clean rooms found in manufacturing, research, and other facilities are typically classified into two broad categories based on the static air pressure inside the rooms relative to atmospheric pressure and/or based on the air pressure in spaces adjacent the clean rooms. A positive air pressure room is maintained at an absolute air pressure greater than atmospheric pressure, greater than the air pressure in spaces adjacent the clean room, or both. The positive air pressure in such rooms is provided by pumping filtered and/or conditioned air into the rooms and controlling the flow of air out of the rooms. The adjacent spaces, which may be manufacturing facilities or offices, are typically maintained at or close to atmospheric pressure by heating, ventilation, and air conditioning (HVAC) systems, or by providing an opening to the environment that allows the adjacent spaces to equilibrate with atmospheric pressure. Thus, air flowing from the positive pressure clean room will flow toward the lower pressure in adjacent rooms or to the atmosphere.

When a positive air pressure clean room is breached, air flowing to adjacent spaces or the atmosphere is generally not a problem as long as airborne contaminants present in the clean room do not pose a potential adverse health effect to people in the adjacent spaces. Typically, the air inside clean rooms in which electronics, aerospace hardware, optical systems, military equipment, and defense-related research are manufactured or conducted may not contain airborne gases, vapors, and particulate matter at concentrations that present a safety or health concern to human health or the environment. However, that is not always the case, as other operations within those industries may generate contaminants that are above acceptable levels and, therefore, must be prevented from escaping the clean room without treatment.

A negative air pressure room is maintained at an absolute air pressure that is either less than atmospheric pressure, less than the air pressure in spaces adjacent the clean room, or both. The negative pressure is maintained by pumping air out of the room at a rate faster than that at which filtered and/or conditioned air is pumped into the room. Negative pressure rooms are often used when there is a concern that contaminants in the air in the room may pose a potential health threat to human health in adjacent spaces or the environment.

Notwithstanding the human health and environmental implications, certain types of manufacturing and research operations must be conducted within a positive air pressure clean room to satisfy regulatory requirements and industry-adopted good manufacturing and laboratory quality control standards. For example, state and federal regulations, including those promulgated by the National Institute for Occupational Safety and Health (NIOSH), may necessitate the use of positive or negative pressure clean rooms.

In particular, the U.S. Food & Drug Administration (FDA) requires that pharmaceutical production be performed within the confines of clean rooms that provide for the validation and certification that manufactured batches of pharmaceutical products are being produced in a sanitary environment. Various FDA regulations and standards also specify requirements for air sampling and/or air monitoring equipment to be used inside clean rooms to verify or validate the cleanliness of the facility during certain drug manufacturing activities. The regulations also provide for electronic data recording, accuracy, precision, and record-keeping relating to monitoring the air quality within clean rooms. Similar requirements are imposed on other industries, such as the biotechnology industry.

Current systems for testing and monitoring the air quality in controlled environments include a plurality of sterlizable microbial atriums (SMA) that are connected to a distributed digital control (DDC) control center. An example of an SMA-DDC system includes the SMA-DDC-10 and integrated One Touch Control System produced by Veltek Associates Inc. of Malvern, Pa. Other systems are shown in U.S. Pat. Nos. 8,169,330; 7,973,668; 7,940,188; and 8,188,874, the disclosures of which are hereby incorporated by reference. Such systems typically include a hardware-based interface that allows users to interface with the air sampling equipment.

A disadvantage associated with conventional air sampling systems is that, because the HCI is hardware-based, it is often difficult and expensive to customize or change. For example, it may be difficult or expensive for a user to increase or decrease the number of monitoring locations based on changes to the user's needs Accordingly, a need exists for a system for controlling air sampling in controlled environments that is flexible, cheaper to implement feature changes, and provides a consistent user interface.

SUMMARY OF THE INVENTION

In accordance with an aspect of the present invention there is provided a system for sampling air at multiple locations in a controlled environment. The system includes one or more air sampling devices configured to monitor and test a volume of air within a controlled environment. A control center including a programmable logic controller (PLC) is configured to monitor and control the one or more air sampling devices. One or more touch panel displays are connected to the control center and provide a human-computer interface between the control center and users.

BRIEF DESCRIPTION OF THE DRAWINGS

For the purpose of illustration, there are shown in the drawings certain embodiments of the present invention. In the drawings, like numerals indicate like elements throughout. It should be understood that the invention is not limited to the precise arrangements, dimensions, and instruments shown. In the drawings.

DETAILED DESCRIPTION OF THE INVENTION

Figure 1:
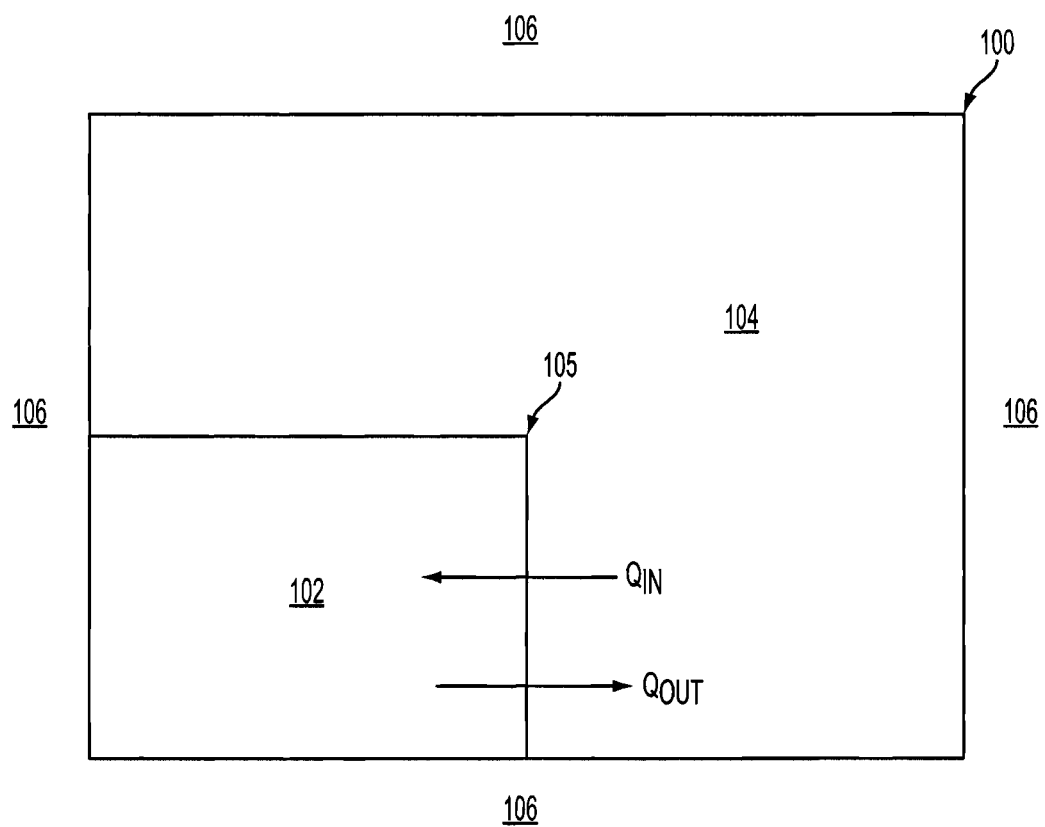
FIG. 1 is a schematic diagram of an exemplary facility having a clean room therein, in accordance with an exemplary embodiment of the present invention.

None of the conventional devices described above provide a high degree of flexibility to rearrange a display to show any number of individual parameters associated with air sampling and monitoring including, but not limited to, the location name, sample time, or duration of air quality tests. Because these conventional devices are not programmable, as new features are created, physical changes to the hardware are required. Additionally, none of the conventional devices described above allow for the collection of time sample data. The present invention overcomes these shortcomings by providing a flexible, programmable air sampling and monitoring system that includes a programmable logic controller-based control center and a plurality of associated touch panel displays sharing a unified interface.

The present invention will be explained in terms of exemplary embodiments. This specification discloses one or more embodiments that incorporate the features of this invention. The disclosure herein will provide examples of embodiments, including examples of data analysis from which those skilled in the art will appreciate various novel approaches and features developed by the inventors. These various novel approaches and features, as they may appear herein, may be used individually, or in combination with each other as desired.

In particular, the embodiment(s) described, and references in the specification to "one embodiment", "an embodiment", "an example embodiment", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, persons skilled in the art may affect such feature, structure, or characteristic in connection with other embodiments whether or not explicitly described.

Embodiments of the invention may be implemented in hardware, firmware, software, or any combination thereof, or may be implemented without automated computing equipment. Embodiments of the invention may also be implemented as instructions stored on a machine-readable medium, which may be read and executed by one or more processors. A machine-readable medium may include any mechanism for storing or transmitting information in a form readable by a machine (e.g. a computing device). For example, a machine-readable medium may include read only memory (ROM); random access memory (RAM); hardware memory in PDAs, mobile telephones, and other portable devices; magnetic disk storage media; optical storage media; flash memory devices; electrical, optical, acoustical, or other forms of propagated signals (e.g. carrier waves, infrared signals, digital signals, analog signals, etc.), and others. Further, firmware, software, routines, instructions, may be described herein as performing certain actions. However, it should be appreciated that such descriptions are merely for convenience and that such actions in fact result from computing devices, processors, controllers or other devices executing the firmware, software, routines, instructions, etc.

The present invention will be described in terms of one or more examples, with reference to the accompanying drawings. In the drawings, like reference numbers indicate identical or functionally similar elements. Additionally, the left-most digit(s) of most reference numbers may identify the drawing in which the reference numbers first appear. Several exemplary embodiments of the invention are described for illustrative purposes, it being understood that the invention may be embodied in other forms not specifically shown in the drawings.

Turning first to FIG. 1, shown therein is a schematic of an exemplary facility 100 having one or more clean rooms 102 therein, in accordance with an exemplary embodiment of the present invention. The clean room 102 is surrounded by an adjacent space 104 and the outdoor atmosphere 106. The adjacent space 104 may be one or more rooms within the same facility 100 in which the clean room 102 is located and that adjoin the clean room 102, such as, for example, a separate manufacturing room, another clean room, a finish and fill room, a research laboratory, offices, etc. The clean room 102 and adjacent space 104 are separated by a divider, such as a wall 105.

The clean room 102 in the exemplary facility 100 is capable of being maintained at an air pressure $P_1$ that is less than or greater than the air pressure $P_2$ of the adjacent space 104 and atmospheric air pressure $P_{ATM}$ of the outdoor atmosphere 106. That is accomplished by an HVAC system (not shown) that causes conditioned and filtered air to be pumped into the clean room 102 at a controlled flow rate $Q_{IN}$ as depicted in FIG. 1. Air inside the clean room 102 that is pumped out of or otherwise flows out of the clean room 102 is represented by $Q_{OUT}$. When the difference between $Q_{IN}$ and $Q_{OUT}$ (i.e., $Q_{IN}-Q_{OUT}$) is greater than zero, a positive pressure will be maintained in the clean room 102. And, when the difference between $Q_{IN}$ and $Q_{OUT}$ is less than zero, a negative pressure will be maintained in the clean room 102.

Figure 2:
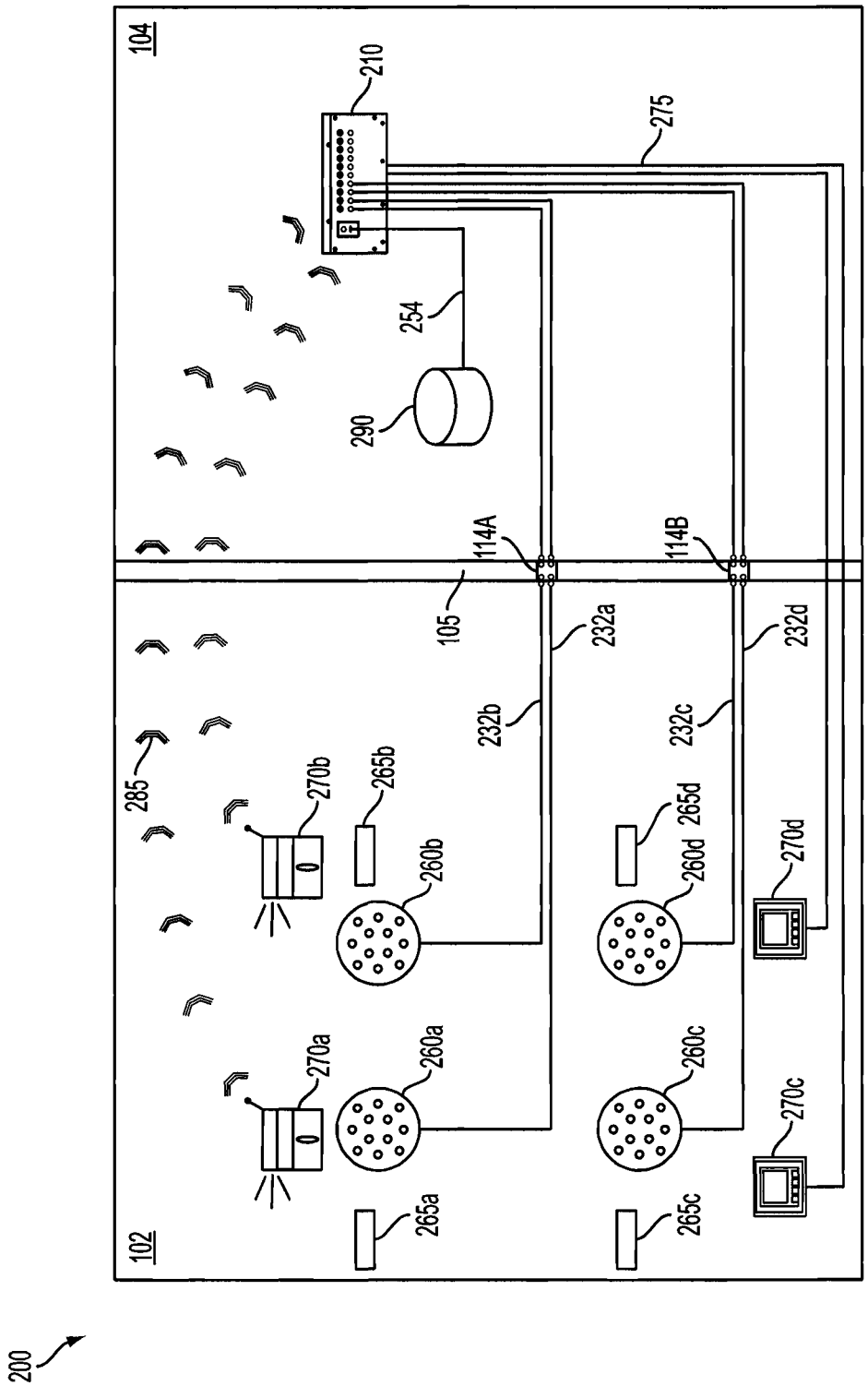
FIG. 2 is a schematic diagram of a tracking/logging and air sampling/monitoring system for use in the clean room of FIG. 1 that includes a PLC-based control center and one or more associated touch panel displays, in accordance with an exemplary embodiment of the present invention.

Turning now to FIG. 2, shown therein is a schematic diagram of an air sampling/monitoring system 200, in accordance with an exemplary embodiment of the present invention. The system 200 generally includes a control center 210, air sampling devices 260, and user interfaces or touch panels 270. The control center 210 and the touch panels 270 can include processors, displays, wireless devices, and memory to operate in accordance with the invention. The touch panels 270 can be wall-mounted, desktop, portable, or a combination.

The system 200 is configured for use in tracking and logging data obtained from a plurality of air sampling devices. During air sampling, air from the clean room 102 is drawn through the air sampling devices 260a-d of the system 200 to collect contaminants present in the air of the clean room 102. An air sampling device 260 is shown, for instance, in U.S. Publication No. 2011/0167931, the content of which is hereby incorporated by reference. The data acquired about the air sampling devices 260a-d is used to monitor and gather airborne particle count and other parameter levels in the clean room 102 in order to maintain the integrity of experiments or production processes therein.

The system 200 includes a control center 210, which may be located in the adjacent space 104 or adjacent to or remote from (i.e., not directly adjacent to) the clean room 102. The control center 210 may include modular ports, such as the modular ports described and illustrated in the '330 patent, where each of such ports may be connected to a vacuum air line. Using these ports, the control center 210 can be configured to draw in air from the air sampling devices 260a-260d and to provide for the air sampling performed by the air sampling devices 260a-260d. The vacuum air lines may be connected across the wall 105 via a wall-mounted quick disconnect outlet, where the outlets and are located on the wall 105 in between the clean room 102 and the adjacent space 104.

The system 200 further includes a plurality of air sampling devices 260a, 260b, 260c, and 260d, all of which may be co-located together in the clean room 102. In the exemplary embodiment of the system 200 illustrated in FIG. 2 and described herein, the system 200 comprises four air sampling devices 260a-260d. It is to be understood that the number of air sampling devices 260a-260d is not limited by the system 200 to any particular quantity of air sampling devices 260. That is, the system 200 is scalable to substantially any number, n, of air sampling devices 260. The air sampling devices 260a-260d may be any known air sampling device for collecting a volume of air. An example of an air sampling device suitable for use as the air sampling devices 260 is described in the '330 patent, the contents of which are incorporated herein by reference.

The system 200 further includes subjects 265a, 265b, 265c, and 265d, which are located at various sites within the clean room 102. The air sampling devices 260a-260d are positioned to collect airborne contaminants in the clean room 102, and can be positioned, for instance, adjacent to one or more of the subjects 265a-265d, where the subjects 265 can be equipment, personnel, etc. Specifically, the air sampling devices 260a-260d can be used to collect the air surrounding respective subjects 265a-265d, i.e., to draw air over the subjects 265a-265d during air sampling, so that contaminants in the air of the clean room 102 at sites of interest are collected by the air sampling devices 260a-d.

The control center 210 may connect to a vacuum pump (not shown), additional vacuum air lines (not shown), or other equipment, illustration of which is omitted herein for clarity. The control center 210 is used to turn on the air flow to each air sampling device 260a-260d so that any combination of the air sampling devices 260a-260d can be employed simultaneously to perform sampling cycles at various locations throughout the clean room 102. In one exemplary embodiment, the control center 210 is configured so that each air sampling device 260a-260d processes 1 CFM (28.3 liters/min) of air, which is the desired air flow rate needed to conduct a proper sampling cycle.

In another exemplary embodiment, the control center 210 is configured to allow for the air flow rates to be individually set, as described below. The control center 210 communicates data and commands from the touch panels 270 and the air sampling devices 260a-260d. The control center 210 is connected to each of the air sampling devices 260a-260d via respective vacuum connections 232a, 232b, 232c, and 232d. The vacuum connections 232a and 232b are connected across the wall 105 via a connector 114A, and the vacuum connections 232c and 232d are connected across the wall 105 via a connector 114B.

It is to be understood, however, that the control center 210, the touch panels 270, and the air sampling devices 260a-260d communicate with one another in any suitable manner. For example, in an exemplary alternative embodiment, the touch panels 270 have network addresses, and the control center 210 communicates with the different touch panels 270 by use of those network addresses via a common connection (e.g. an Ethernet network or wireless local area network (LAN)).

The exemplary embodiment of the system 200 illustrated in FIG. 2 illustrates four vacuum connections 232a-232d, each of which corresponds to a respective one of the air sampling devices 260a-260d. It is to be understood that the number of vacuum connections 232a-232d is not limited by the system 200 to any particular quantity of connections. That is, the system 200 is linearly scalable to substantially any number, n, of vacuum connections 232a-232n. Furthermore, although the control center 210 and the touch panels 270 are shown in wired communication with one another, it is to be appreciated that these components of the system 200 may communicate wirelessly in an alternative exemplary embodiment of the system 200.

The control center 210 includes interfaces for interfacing with the touch panels 270a-d, and the control center 210 includes interfaces for interfacing with the air sampling devices 260a-260d. The control center 210 detects conditions (e.g., flow rates, alarm conditions, etc.) and issues commands (e.g., to start and/or stop air flow) with the air sampling devices 260a-260d via respective vacuum connections 232a-232d. The control center 210 also receives data and commands from the touch panels 270a-270d over respective connections 275 and 285. Various examples of data and commands transmitted by the touch panels 270a-d, the air sampling devices 260a-d, and the control center 210 are described below.

In one exemplary scenario, a first touch panel such as touch panel 270a may be located near a first air sampling device such as air sampling device 260a and away from a second air sampling device such as air sampling device 260b. By interacting with the interface presented by the first touch panel 270a, the user may cause a signal to be sent to the control center 210 for thereby controlling or monitoring the second air sampling device 260b. Thus, any air sampling device 260a-d may be controlled or monitored using any touch panel 270a-d irrespective of where they are located.

In another exemplary scenario, an alarm may be generated by a first air sampling device 260a and a notification of the alarm may be presented to one or more of the touch panels 270a-d irrespective of their locations. For example, in the exemplary configuration shown in FIG. 2, an alarm generated by the air sampling device 260a may be detected by the control center 210 and then information associated with the alarm may be relayed to one or more of the remotely-located touch panels 270b-d, instead of or in addition to the adjacent touch panel 270a. In this way, important alarm information may be automatically presented to the location(s) where users are located when the alarm is detected rather than being presented only at the location of the alarm, where users may or may not be located. It will be recognized, however, that the touch panels 270 can directly communicate with one another, such as to de-activate an alarm signal.

As mentioned above, the present invention overcomes the shortcomings of conventional air monitoring systems having hardwired components by providing a more flexible and programmable air sampling and monitoring system that includes a programmable logic controller-based control center and a plurality of associated touch panel displays sharing a unified interface. The programmable logic controller (PLC) is a digital computer used for automation of electromechanical processes, including control of machinery, such as the sterilizable microbial atriums (SMAs) described herein. Unlike general-purpose computers, the PLC is designed for multiple inputs and output arrangements, extended temperature ranges, immunity to electrical noise, and resistance to vibration and impact. The PLC can be programmed using application software executed on separate general purpose computers. Such a computer may be connected to the PLC through Ethernet, RS-232, RS-485, RS-422, or other suitable communications cabling. Generally, the programming software provides functions for debugging and troubleshooting the PLC software, for example, by highlighting portions of the logic to show current status during operation or via simulation. The software can upload and download the PLC program for backup and restoration purposes. In some PLC embodiments, the program is transferred from a personal computer to the PLC through a programming board which writes the program into a removable chip such as an EEPROM or EPROM. PLCs may be used to interact with users for the purpose of configuration, alarm reporting or everyday control. A human-machine interface (HMI) is employed for this purpose. HMIs are also referred to as a human-computer interface (HCI), a man-machine interface (MMI) and a graphical user interface (GUI). A simple system may use buttons and lights to interact with the user. Text displays are available as well as graphical touch screens.

The control center 210 may communicate data and commands provided by the touch panels 270 and the air sampling devices 260a-260d for tracking and monitoring the system 200 in real time and logging the data and commands in a database 290 maintained by the control center 210. Although the system 200 is described and illustrated herein as including the database 290, it is to be understood that the system 200 is not so limited. In other exemplary embodiments, the element 290 is a spreadsheet, a flat text file, or other data structure stored in a computer-readable medium.

The air sampling devices 260a-260d are configured to independently monitor various data during operation, e.g., during air sampling. Such data include any flow rates sensed by the respective air sampling devices 260a-260d, alarm signals generated by the respective touch panels 270, etc. For example, the touch panels 270 monitor and display the actual flow rate that is realized at their respective air sampling devices 260a-260d. If the flow rate is off by +/−0.5% (i.e., not within the range of 0.95-1.05 CFM or 26.9-29.7 liters/min), then the corresponding air sampling device 260a-260d may generate an alarm signal.

An additional aspect of this exemplary embodiment provides that the control center 210 communicates any data and alarm signals received from the touch panel 270 to one or more of the other touch panels 270, so that they may activate their respective visual alert indicators and audible alarms. The data and alarm signals can be independently monitored and controlled by the control center 210.

In one embodiment, when a low flow rate is detected in one of the air sampling devices 260a-260d, such as when a detected flow rate falls below 1 CFM or any other suitable and configurable threshold value, the control center 210 may provide one or more types of alarms for alerting a user of the low flow condition. For example, lights or sounds may be activated including strobe lights, colored lights, sirens, and pre-recorded audio files. Additionally or alternatively, with the PLC-based control center 210, an escalation protocol may be implemented whereby a predefined sequence of steps may be taken in response to the failure of a user to address/stop the alarm within predefined time period(s). For example, immediately after an initial alarm condition has been triggered, a visual map of the location of the low flow may be shown and/or highlighted within the context of the facility. If the alarm should continue without user acknowledgement (ACK), the next step in the escalation protocol may be performed. If after five minutes no ACK is received, an email may be sent to an administrator or other designated user(s). If after ten minutes no ACK is received, an email may be sent to an expanded list of users/administrators. If after fifteen minutes no ACK is received, a simple message service (SMS) text message may be sent to one or more users. If after twenty minutes no ACK is received, a phone call may automatically be placed to one or more users and a designated pre-recorded sound file may be played. If still no ACK is received, a message may be sent to a different user or set of users located remotely from the facility who are dedicated to responding to such alarms.

During operation, the control center 210 also monitors data relating to air sampling. For example, the control center 210 monitors flow rates through the ports of the control center 210, whether the individual ports of the control center 210 are powered up, and whether the ports are in an air sampling mode and/or are experiencing an air flow error during an air sampling cycle. The control center 210 may transmit any such data to the touch panels 270.

Thus, as depicted in FIG. 2, the system 200 further includes one or more touch panels 270, which are connected to the control center 210 via a wired or wireless connection 275, 285. The touch panel 270 may be co-located with the air sampling devices 260a-260d in the clean room 102, as shown in FIG. 2, or co-located with the control center 210, or otherwise located outside of the clean room 102. Thus, although the touch panels 270 are each preferably located proximal to a respective air sampling device 260, they need not be. Rather, the touch panels 270 can be located remote from all of the air sampling devices 260.

The touch panel 270 includes an interface for communicating with the control center 210 for receiving data from the control center 210 and providing commands to the control center 210 for relaying to their proper destinations. It is to be understood that the touch panel 270 may be configured to receive any data and commands provided to the control center 210 described herein.

For example, when the control center 210 and the touch panel 270 communicate, the touch panel 270 may receive data from the control center 210 collected during an air sampling period. As described above, such data may indicate whether the individual ports of the control center 210 are powered up, are in an air sampling mode, and/or experience an air flow error during an air sampling cycle. In that way, the touch panel 270 can detect the state of activity of each of the individual ports of the control center 210, thereby allowing a user to determine where in the facility 100 air sampling is being conducted (i.e., which air sampling devices 260a-260d are presently being operated, the time associated with a sampling cycle, etc.) and at which air sampling devices 260a-260d any errors occur. Such data may further indicate the flow rates sensed in the air sampling devices 260a-260d, alarm conditions in the air sampling devices 260a-260d, etc. Thus, the touch panel 270 may be used to display data, e.g., data collected during an air sampling period or other data described below, in real time regarding components of the system 200.

The touch panel 270 may also be configured to provide commands to components of the system 200, such as the air sampling devices 260a-260d and the control center 210. For example, the touch panel 270 can also be used to remotely start and stop sampling at various air sampling devices 260a-260d within the facility 100, thereby eliminating the need for the user to access the control center 210 to perform these functions. Thus, in an exemplary embodiment, the touch panel 270 includes various input means, such as a touch screen that receives input from a user to signal to the control center 210 which air sampling devices 260a-260d to operate. The touch panel 270 communicates such commands to the control center 210, thereby eliminating the need for the user to leave the location (room) of the touch panel 270 to operate the control center 210 or the air sampling devices 260a-260d.

In an exemplary embodiment, the control center 210 monitors conditions in the clean room 102 and may monitor conditions in other rooms, e.g., other clean rooms 102 or rooms 104. The control center 210 includes software that includes a graphical representation of the different components of the system 200. The control center 210 and/or the touch panels 270 may include software to render such representations, receive real-time data from the control center 210 for these components, and display the real-time data.

The control center 210 may also be configured to collect and store data regarding the operation of the components of the system 200 and commands provided by components of the system 200. Data recorded by the control center 210 may include data obtained during an air sampling period (the period of time over which the subjects 265a-265d collect airborne contaminants from a clean room, such as the clean room 102) and data obtained during an incubation period. Such data may include data scanned by a barcode scanner, data inputted by a user, and data monitored by the air sampling devices 260a-260d and the control center 210. The control center 210 stores data and commands in the database 290 or other memory.

Data obtained during an air sampling period may include any of the following data: (1) identification data of the subjects 265a-265d; (2) location data of the subjects 265a-265d; (3) the date and time such location data was obtained; (4) identification data of the user; and (5) the date and, optionally, time the subjects 265a-265d expire. Data obtained during the air sampling period may also include any of the following monitored data: (1) the flow rate at each individual air sampling device 260a-260d; (2) the dates and times of the measured flow rates; (3) flow alerts/alarms generated at the air sampling devices 260a-260d; (4) indications of whether the individual ports of the control center 210 are powered up; (5) indications of whether the individual ports of the control center 210 are in an air sampling mode; (6) air flow errors detected by the control center 210; (7) flow rates detected by the control center 210; (8) identification data of the air sampling devices 260a-d; and (9) location data of the air sampling devices 260a-d.

Data obtained during the incubation period can include any of the following: (1) identification data of the subjects 265a-265d obtained by a barcode scanner; (2) location data of the subjects 265a-265d obtained by or generated by the barcode scanner; (3) the date and time such location data was obtained, i.e., when the scan was performed; (4) identification data of the person operating the barcode scanner; (5) and remarks entered by a user. It is to be understood that the date and time data for the scan may be automatically generated by an internal electronic clock within the touch panel 270 or the control center 210. Alternatively, such date and time data may be manually entered by the user. The data may also include the same data obtained during the air sampling period above.

The control center 210 is the gateway of data and commands received from the various components of the system 200, which may log the data and commands in the database 290 for later retrieval and/or which may provide real-time monitoring and display by the control center 210. In an additional exemplary embodiment, the touch panel 270 may access the historical data, such as past identification data, location data, dates, times, etc., logged by the control center 210 in the database 290. Using the touch panel 270, an operator may request information about a selected subject 265a-265d or the respective air sampling devices 260. The touch panel 270 receives such selection and forwards it to the control center 210. The control center 210 responds with the desired current and/or historical data. For example, using the touch panel 270, the operator can select one of the subjects 265a-265d or air sampling devices 260a-260d. The control center 210 responds with identification data, historical location data, historical times and dates of scans, etc. for the selected subject 265a-265d or air sampling device 260a-260d. The touch panel 270 displays such historical data.

To facilitate the real-time monitoring of the system 200 and the logging of data regarding the system 200, the control center 210 includes any suitable computing processor or processing platform that is capable of performing the functions and operations of the exemplary embodiments of the control center 210 described herein, e.g., real-time monitoring of data and commands in the system 200, tracking and logging of data and commands of the system 200 in the database 290, and recalling of historical data stored in the database 290. The control center 210 can include a computer-readable medium comprising software code stored thereon that, when executed by the control center 210, causes the control center 210 to perform any of the functionality of the control center 210 described herein. Thus, all or parts of the functionality of the control center 210 that provide for remotely monitoring the system 200, storing data and commands in the database 290, and retrieving stored (historical) data from the database 290 may be stored as computer-readable software instructions in a computer-readable media and retrieved from the computer-readable media and executed to perform the functions of the control center 210 described herein.

The computing platform for the control center 210 is desirably a PLC-based computer or server, either in a stand-alone system or as part of a network. It is to be understood that the control center 210 can be connected to any number of systems 200 at any number of locations, thereby providing a mechanism for monitoring and controlling multiple clean rooms 102 from a single, central location. And, the same functionality may be provided via a secure website from which a user can remotely monitor and control any number of systems 200 over the Internet from virtually any location, adding yet another degree flexibility and accessibility to the present invention. Thus, for instance, control center 210 can alert users in a first clean room of an alarm condition at an air sampling device 260 located in a second clean room that is separate and remote from the first clean room; and the user in the second clean room monitor air sampling devices 260 in the first clean room and clear alarm conditions in the first clean room. In a further embodiment, touch panels 270 in the first clean room can communicate with touch panels 270 in the second clean room, as desired.

Figure 3:
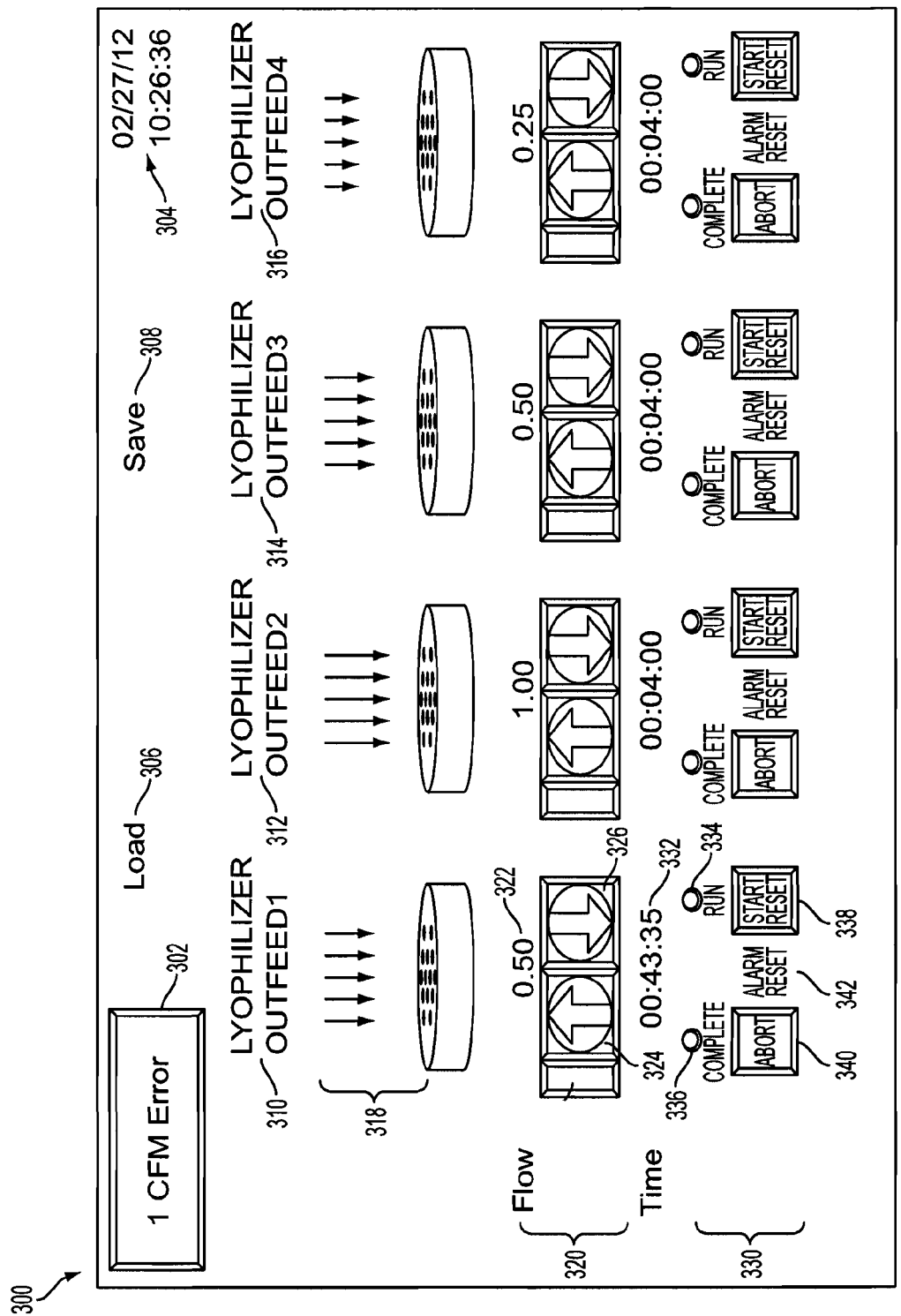
FIG. 3 is a screenshot of an exemplary human computer interface that may be displayed on a touch panel display for monitoring or controlling one or more air sampling devices via the control center, in accordance with an exemplary embodiment of the present invention.

Turning to FIG. 3, the human computer interface 300 displayed on touch panels 270 is shown in greater detail. The interface illustrated in FIG. 3 includes interface elements for measuring, monitoring, and controlling the flow rate, as well as detecting airflow errors during a sampling cycle at each of the air sampling devices 260a-260d.

For example, the interface 300 may include a display that can be read from multiple angles and distances and various buttons or other user interface elements that allow the user to monitor or adjust the various features of the air sampling devices 260a-260d. Accordingly, providing a consistent interface 300 for each of a number n of corresponding air sampling devices 260a-260d, each touch panel 300 may be provided at a location where the air sampling devices 260a-260d located throughout a clean room 102 can be measured, monitored, and controlled.

Referring to FIG. 3, the interface 300 includes various touch-sensitive screen portions for providing various functions and information to users, which may hereinafter also be referred to as "buttons." For example, button 302 may indicate an alarm condition such as whether the current flow rate is outside of an acceptable flow rate error threshold value (e.g., 1 CFM). By pressing the button 302, the user may adjust this value for one or more of the air sampling devices 260. The button 304 may also display the current date and time. Similarly, by pressing the button 304, the user may adjust the format and/or values of the date and time displayed. The buttons 306 and 308 allow the user to load and to save, respectively, configuration or other data in order to be exported and analyzed by another system.

Columns 310, 312, 314, and 316 are each associated with a different air sampling device 260a-260d or monitored zone. As shown, columns 310-316 are associated with Lyophilizer Outfeeds 1-4, respectively. An image/icon 318 may be associated with each of the columns 310-316 for indicating a flow rate for each air sampling device 260a-260d. The icon 318 may also be animated to further enhance the readability of the flow rate indication for users. In the embodiment shown, each icon 318 includes five downward facing arrows, where the length of each arrow provides a visual indication of the flow rate. Longer arrows may indicate higher flow rates, while shorter arrows may indicate lower flow rates. Additionally, the direction of the arrows indicates the directionality of the airflow, where downward animated arrows may indicate an out-feed of air and upward animated arrows may indicate an in-feed of air. If a zone 310-316 or an air sampling device 260 is off, then the corresponding icon 318 may also be off/not shown for the affected zone 310-316.

Buttons and informational icons associated with the flow rates for each of the zones 310-316 are shown in row 320. For example, flow rate indicator 322 shows the current flow rate, such as 1.0 CFM. The flow rate for one or more air sampling devices 260a-260d can be changed by pressing the up/down arrows 324 and 326, respectively, to increase or decrease the value that is displayed, which is then transmitted to the control center 210 so that the desired flow rate being displayed is implemented.

Row 330 shows information and controls associated with the initiation and status of an air sampling test cycle as well as any alarms. For example, time indicator 332 displays the amount of time associated with a currently active or most recently completed air sampling test cycle. As shown by time indicator 332, an air sampling test cycle has forty three minutes and thirty five seconds left for zone 310. Indicator 334 indicates whether an air sampling test cycle is currently in progress (e.g., light on indicates a test in progress, light off indicates no test in progress). Similarly, indicator 336 indicates whether an air sampling test cycle is complete (e.g., light on indicates a test is complete, light off indicates a test is not yet complete).

The start/reset button 338 is utilized to initiate or re-initiate a sampling cycle for an air sampling device 260a-260d, where the sampling cycle continues until the user decides to abort the sampling cycle by pressing the abort button 340. In one embodiment, a typical sampling cycle may last between 10 minutes and 3 hours.

In the event that an alarm or other error condition is detected, the control center 210 may generate an alert/alarm, such as when the flow measured for an air sampling device 216a, 216b, 216c, or 216d is outside of a desired flow rate. Each touch panel 270 may include a visual alert indicator for each air sampling device 260a-260d, as indicated by columns 310-316, where the visual alert indicators indicate if the air flow for a specific air sampling device 260a-260d is outside of the desired flow rate.

As mentioned above, the control center 210 may be configured to activate an alarm when a predetermined alarm condition has been satisfied. The interface 300 also includes an alarm reset button 342. The alarm reset button 342 allows a user to manually reset (i.e., turn off) all of the visual alert indicators after identifying the air sampling devices 260a-260d at which errors occurred during a sampling cycle.

In one embodiment, the predetermined alarm condition may include when the actual rate of air flow at the one or more air sampling devices 260a-260d deviates a predetermined amount from a desired rate of air flow. In such an event, the control center 210 may be configured to activate a visual alarm, such as a strobe and/or colored lights. Thus, for instance, the user interface 300 for a first touch panel 270a proximal to a first air sampling device 260a, can receive the status of the air sampling devices 260a-d from the central control center 210; and display that status in columns 310, 312, 314, 316, respectively. That first user interface 300 can also be used to control the air sampling devices 260a-d (e.g., turn ON/OFF, clear an alarm, etc.) by communicating a command signal to the central control center 210. And, that first user interface 300 can send a command signal to the other touch panels 270a-d, directly or preferably via the control center 210, such as to clear an alarm.

In addition to the visual alarm, the control center 210 may be configured to activate an audio alarm. For example, the audio alarm may include one of a siren and a pre-recorded audio file. Activating the alarm can also include activating an escalation protocol whereby a predefined sequence of steps are taken in response to the failure of a user to acknowledge the alarm within one or more predefined time periods. For example, at a first step in the escalation protocol, activating the alarm includes providing a visual map of the location of the alarm condition at one or all of the touch panels 270. If the alarm is not acknowledged, such as by pressing the alarm reset button 342 on the touch panel 270, an email may be sent to one or more designated users. A third step in the escalation protocol may include sending a simple message service (SMS) text message to a user's mobile device. If the alarm is still not acknowledged, a phone call may be automatically placed to one or more users and playing a designated pre-recorded sound file. Finally, a message may be sent one or more users located remotely from the facility associated with the alarm in order to address the detected alarm condition.

It is appreciated that, in some embodiments, the audible alarm may continue until the error conditions are removed or acknowledged yet the visual alert indicator may remain on even after the error conditions are removed or acknowledged. This allows a user to determine, sometime after the alarm signal was generated and/or after the sampling cycle, which of the multiple air sampling devices 260a-260d experienced an error condition during the sampling cycle. Accordingly, the user to can remain focused on his or her work in the clean room 102 rather than having to immediately check which air sampling device 260a-260d is experiencing errors every time an audible error alert sounds. If all of the error conditions have been removed and all of the flow rates have returned to the desired level, all of the visual alert indicators will turn off. For any air sampling devices 260a-260d for which an error condition still exists, the visual alert indicator may remain on.

It is appreciated that one advantage of the present invention includes simplifying the configuration of the air sampling devices and related components necessary for monitoring and controlling air sampling in a controlled environment by avoiding the need for certain components, such as conventional flow switches. The present invention also provides a high degree of flexibility to rearrange a display to show any number of individual parameters associated with air sampling and monitoring including, but not limited to, the location name, sample time, or duration of air quality tests. Because conventional devices are not PLC-based and therefore are not programmable, as new features are created, physical changes to the hardware are required and do not allow for the collection of time sample data. The present invention overcomes these shortcomings by providing a flexible, programmable air sampling and monitoring system that includes a programmable logic controller-based control center and a plurality of associated touch panel displays sharing a unified interface.

These and other advantages of the present invention will be apparent to those skilled in the art from the foregoing specification. Accordingly, it is to be recognized by those skilled in the art that changes or modifications may be made to the above-described embodiments without departing from the broad inventive concepts of the invention. It is to be understood that this invention is not limited to the particular embodiments described herein, but is intended to include all changes and modifications that are within the scope and spirit of the invention.

What is claimed is:

1. A system for sampling air at multiple locations in a controlled environment comprising:
   one or more air sampling devices configured to collect air contaminants within a controlled environment;
   a control center including a programmable logic controller (PLC) and configured to monitor and control the one or more air sampling devices; and
   a plurality of touch panel displays connected to the control center for receiving data from the control center regarding the one or more air sampling devices, each of the plurality of touch panel displays comprising an interface for displaying the data.

2. The system of claim 1, wherein each of the plurality of touch panel displays is co-located with the one or more air sampling devices.

3. The system of claim 1, wherein each of the plurality of touch panel displays is located inside a clean room environment.

4. The system of claim 1, wherein each of the plurality of touch panel displays is configured to control at least one of the one or more air sampling devices and the control center.

5. The system of claim 1, wherein each of the plurality of touch panel displays is configured to receive alarms associated with at least one of the one or more air sampling devices and the control center and to display the alarms in the interface of the each of the plurality of touch panel displays.

6. The system of claim 1, wherein each of the plurality of touch panel displays is configured to communicate with a second touch panel display.

7. The system of claim 1, wherein the control center is configured to activate an alarm when a predetermined alarm condition has been satisfied.

8. The system of claim 7, wherein the predetermined alarm condition includes when an actual rate of air flow at the one or more air sampling devices deviates a predetermined amount from a desired rate of air flow.

9. The system of claim 7, wherein the control center is configured to activate a visual alarm.

10. The system of claim 9, wherein the visual alarm includes one of strobe lights and colored lights.

11. The system of claim 7, wherein activating the alarm includes activating an escalation protocol whereby a predefined sequence of steps are taken in response to a failure of a user to acknowledge the alarm within one or more predefined time periods.

12. The system of claim 7, wherein activating the alarm includes providing a visual map of the location of the alarm condition.

13. The system of claim 7, wherein activating the alarm includes sending an email to one or more designated users.

14. The system of claim 7, wherein activating the alarm includes sending a simple message service (SMS) text message.

15. The system of claim 7, wherein activating the alarm includes automatically placing a phone call to one or more users and playing a designated pre-recorded sound file.

16. The system of claim 7, wherein activating the alarm includes sending a message to one or more users located remotely from a facility associated with the alarm.

17. The system of claim 1, wherein the control center is configured to wirelessly communicate with the plurality of touch panel displays.

18. The system of claim 1, wherein the plurality of touch panel displays comprises a first touch panel display located within the controlled environment and a second touch panel display located outside the controlled environment.

19. The system of claim 1, wherein the one or more air sampling devices includes a sterilizable microbial atrium (SMA).

20. The system of claim 1, wherein the control center is in electrical communication with a vacuum source and is configured to control the vacuum source.

21. The system of claim 20, wherein the plurality of touch panel displays is in electrical communication with the control center, and wherein the plurality of touch panel displays is configured to communicate with the control center for controlling the vacuum source so that the vacuum source pulls a predetermined volume of air through at least one of the one or more air sampling devices at a desired rate of air flow.

22. A method for sampling air at multiple locations in a controlled environment, comprising the steps of:
   providing two or more air sampling devices at different locations within the controlled environment;
   providing a control center at a location outside of the controlled environment and in separate air flow communication with each of the two or more air sampling devices;
   providing a plurality of touch panels for the two or more air sampling devices, each of the plurality of touch panels provided at a location between a corresponding air sampling device and the control center, each of the plurality of touch panels being connected to the control center and configured to separately receive data from the control center regarding the two or more air sampling devices and to control the two or more air sampling devices via information exchanged with the control center, each of the plurality of touch panels comprising an interface for displaying the data; and
   automatically activating an alarm at one or more of the plurality of touch panels when the rate of air flow measured at one or more of the two or more air sampling devices deviates from a desired value by a predetermined amount.

23. The method of claim 22, further comprising the step of automatically activating an alarm at a first of the touch panels when the rate of air flow measured at a second of the two or more air sampling devices deviates from the desired value by the predetermined amount.

24. A method for sampling air at multiple locations in a controlled environment, comprising the steps of:
   providing two or more air sampling devices at different locations within the controlled environment;
   providing a control center at a location outside of the controlled environment and in separate air flow communication with each of the two or more air sampling devices;
   providing a plurality of touch panels for the two or more air sampling devices, each of the plurality of touch panels provided at a location between a corresponding air sampling device and the control center, each of the plurality of touch panels being connected to the control center and configured to separately receive data from the control center regarding the two or more air sampling devices and to control the two or more air sampling devices via information exchanged with the control center, each of the plurality of touch panels comprising an interface for displaying the data;

detecting an interaction between the one of the plurality of touch panels and a user; and exchanging information between the one of the plurality of touch panels, the control center, and the one or more air sampling devices in response to the detected interaction.

25. A system for sampling air at multiple locations in a controlled environment comprising:

first and second air sampling devices, each configured to monitor and test a volume of air within a controlled environment;

first and second user interfaces, said first user interface associated with said first air sampling device and said second user interface associated with said second air sampling device; and a controller in communication with said first and second user interfaces, wherein said controller is configured to monitor the first and second air sampling devices and generate an alarm signal at the first or second user interfaces, wherein the first and second user interfaces are configured to receive data from the controller regarding the first and second air sampling devices, and wherein each of the first and second interfaces comprise an interface for displaying the data.

26. The system of claim 25, wherein said controller is configured to detect an alarm condition with said first air sampling device and generate an alarm signal at the second user interface.

27. The system of claim 26, wherein said first user interface is located remote from said second air sampling device, and said second user interface is located remote from said first air sampling device.

28. The system of claim 27, wherein said first user interface is located proximal to said first air sampling device and said second user interface is located proximal to said second air sampling device.

* * * * *